United States Patent [19]

Wiley

[11] 3,958,573

[45] May 25, 1976

[54] ASPIRATOR APPARATUS

[76] Inventor: Corless W. Wiley, 1505 Junior Drive, Dallas, Tex. 75208

[22] Filed: Apr. 3, 1974

[21] Appl. No.: 457,576

[52] U.S. Cl. ............................................. 128/276
[51] Int. Cl.² ........................................ A61M 1/00
[58] Field of Search ........................ 128/276–278, 128/349; 27/24 A; 32/33

[56] References Cited

UNITED STATES PATENTS

| 969,922 | 9/1910 | Tracy | 32/33 |
|---|---|---|---|
| 2,531,730 | 11/1950 | Henderson | 128/276 |
| 2,561,622 | 7/1951 | Grubb | 32/33 |
| 3,084,440 | 5/1963 | Wenof | 32/33 |
| 3,499,393 | 3/1970 | Bent | 32/33 |

FOREIGN PATENTS OR APPLICATIONS

| 796,431 | 6/1958 | United Kingdom | 128/276 |

OTHER PUBLICATIONS

Dental Products Report, Mar.–Apr. 1968, p. 29.
Journal of the American Dental Association, Aug. 1967, p. 544.

*Primary Examiner*—Robert W. Michell
*Assistant Examiner*—Henry S. Layton
*Attorney, Agent, or Firm*—Peter J. Murphy

[57] ABSTRACT

Aspirator and aspirators assemblies, particularly adapted for use by dentists and oral surgeons, include a tubular member having an adaptor tip at one end which is configured to coact with varying sizes of suction hose and/or adaptors whereby the aspirator is readily useable regardless of the type of vacuum utility service provided by the building. The adaptor tip is configured to have a smaller diameter tapered portion to be received in and coupled to a small diameter suction hose, a larger diameter portion at its proximal end dimensioned to be received within and coupled to an intermediate diameter suction hose, and with the larger diameter portion dimensioned to coact with an adaptor dimensioned to be received within and coupled to a large diameter suction hose by means of which the aspirator tip is coupled to such large hose. As an additional feature, the adaptor tip is configured to be received within an elongated convenience handle, with the convenience handle being dimensioned to be received either within the intermediate hose for coupling thereto, or within the adaptor for coupling to a large hose.

6 Claims, 24 Drawing Figures

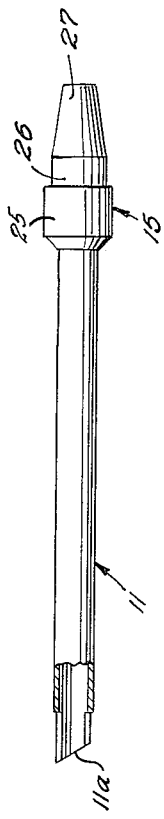
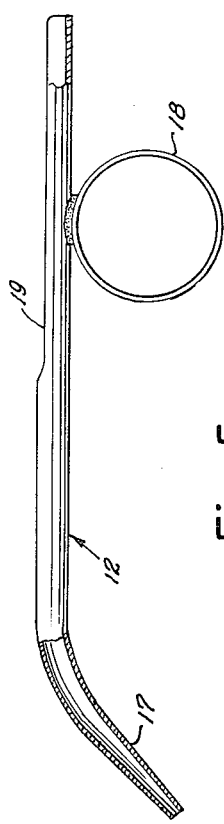
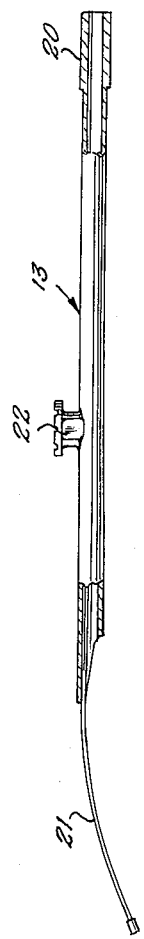
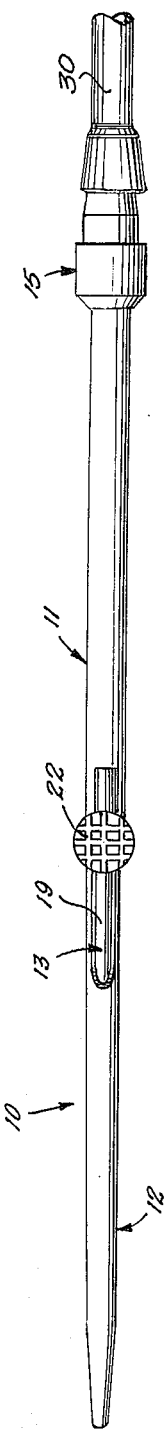
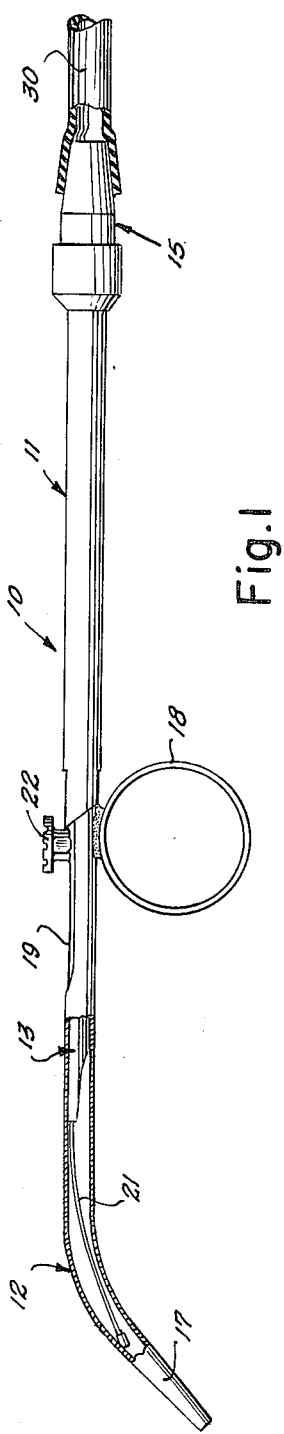

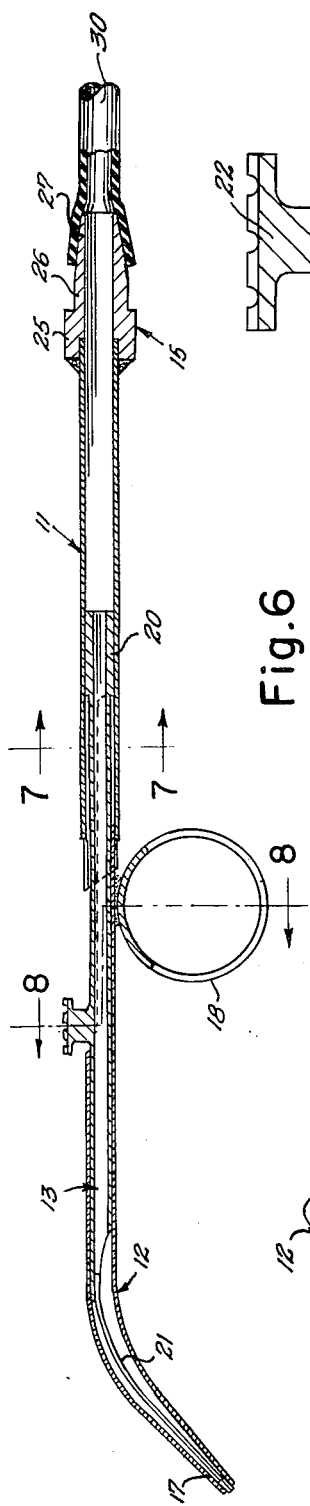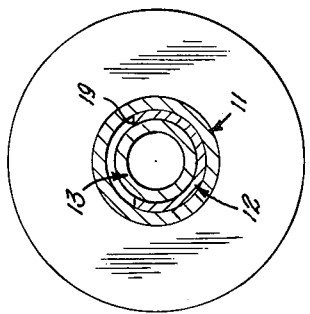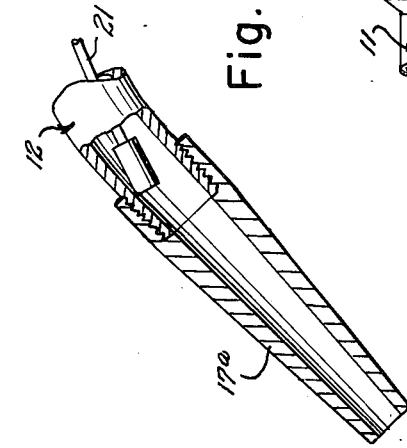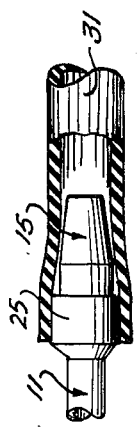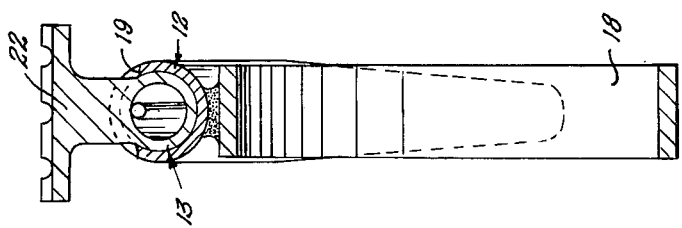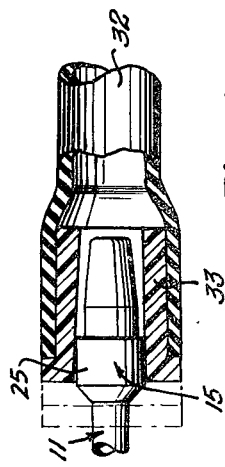

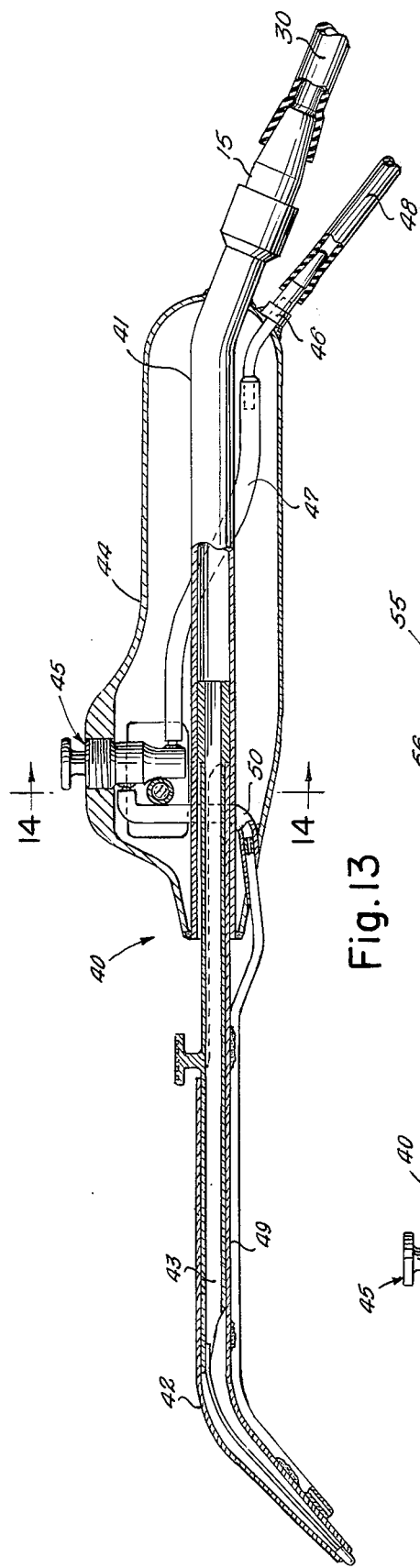
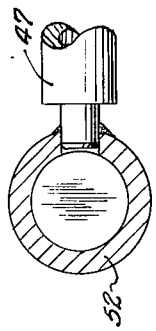
Fig.16
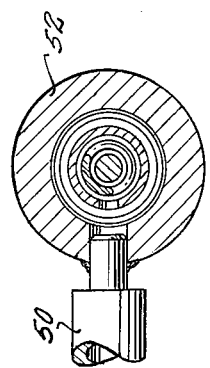
Fig.17
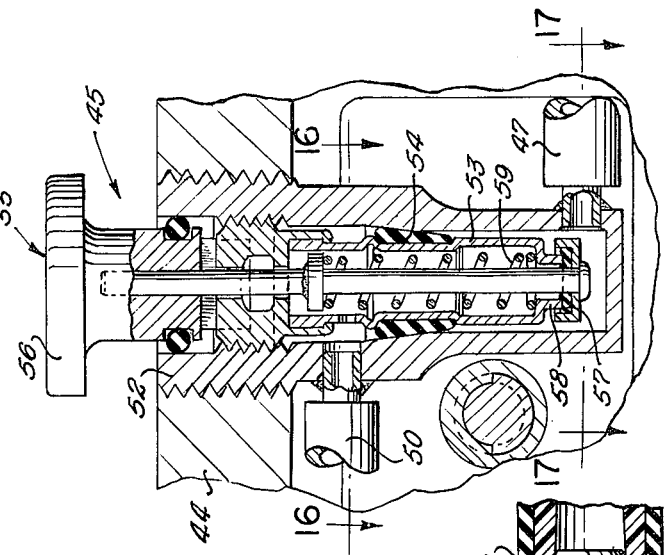
Fig.15
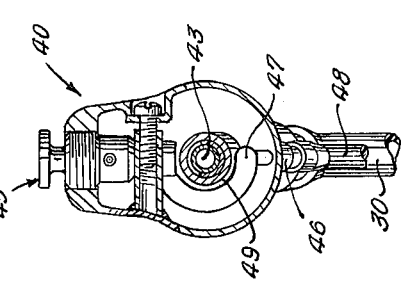
Fig.14
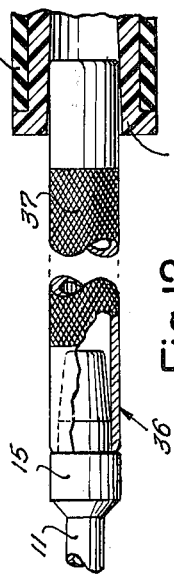
Fig.12

ASPIRATOR APPARATUS

BACKGROUND AND SUMMARY OF THE INVENTION

This invention relates to aspirators and aspirator assemblies, and particularly to such having an adaptor tip configured for coupling to suction hoses of three distinct sizes.

In offices or other buildings provided for use by dentists, oral surgeons, or other medical personnel, these buildings are designed to furnish certain utility services to the several offices, the utility services including fresh water, pressurized air, and vacuum or suction. A difficulty with these utility services (and this invention is principally concerned with the provision of the vacuum or suction service), is that the fittings and connecting hoses are not of standard size so that the supplier of equipment adapted to be attached to such utilities services is faced with the task of providing multiple forms of his devices suitable for use with the several different forms and sizes of service fittings provided.

Where the building facilities occupied by such medical personnel do have built in utilities service, portable systems may be employed; and again these systems do not have standardized fittings so that the utility hoses may be of different size.

The present invention is concerned with evacuation systems, that is utilities systems or services which provide vacuum or suction pressure; and it is common for such systems to employ three different sizes of suction hose which are referred to herein as small hose, medium hose and large hose.

A principal object of this invention is to provide an aspirator having an adaptor tip to enable the coupling of the aspirator to suction hoses of three distinct sizes.

Another object of this invention is to provide an aspirator assembly including separable base, tip, and reciprocating plunger components with the plunger functioning to dislodge tip clogging particles.

Still another object of this invention is to provide an aspirator assembly including separable base, tip, and reciprocating plunger components, wherein the base in separated condition also functions as an aspirator tip.

A further object of this invention is to provide an aspirator tip assembly including a base having an adaptor tip, with the base functioning as a supporting or handle member for other components of aspirator tip assemblies.

A still further object of this invention is to provide an aspirator assembly including separable base, tip, and reciprocating plunger components and also including a wash water conduit and control valve for discharging wash water at the aspirator nozzle.

These objects are accomplished in aspirator apparatus which comprises an elongated tubular member, having an adaptor tip fixed permanently thereto at one end. The adaptor tip has a smaller diameter portion at its distal end, and has an axially extended cylindrical enlargement spaced from the distal end. The smaller diameter portion includes a tapered portion reducing in diameter toward its end, and which is adapted to the received and retained in a small diameter resilient flexible conduit. A tubular adaptor has a slightly tapered internal bore which is dimensioned, in relation to the cylindrical enlargement, for frictional coupling therewith; and has an outer diameter adapted to be received and retained in a large diameter flexible conduit. The adaptor has an external radial flange at one end; and the tapered bore is larger at the flanged end of the adaptor and smaller at the opposite end.

The other end of the tubular member may function as an inlet nozzle for the aspirator apparatus. Also the tubular member may function as a base component for aspirator assemblies including different forms of tip components, which tip components then provide the aspirator inlet nozzles and are coupled to the base component with a sliding friction fit.

The novel features and the advantages of the invention, as well as additional objects thereof, will be understood more fully from the following description when read in connection with the accompanying drawings.

DRAWINGS

FIG. 1 is a side elevation view, partially in section, of an aspirator assembly with a plunger in a retracted position;

FIG. 2 is a top view of the aspirator assembly of FIG. 1;

FIGS. 3, 4 and 5 are side elevational views partially in section, of the plunger, base, and tip components respectively of the aspirator assembly of FIG. 1;

FIG. 6 is a longitudinal sectional view of the assembly of FIG. 1, showing the plunger and stylette in forward position;

Figure 18:
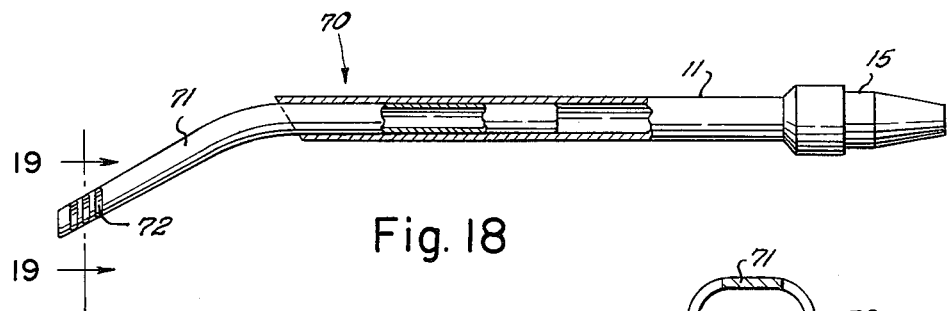
Figure 19:
Figure 20:
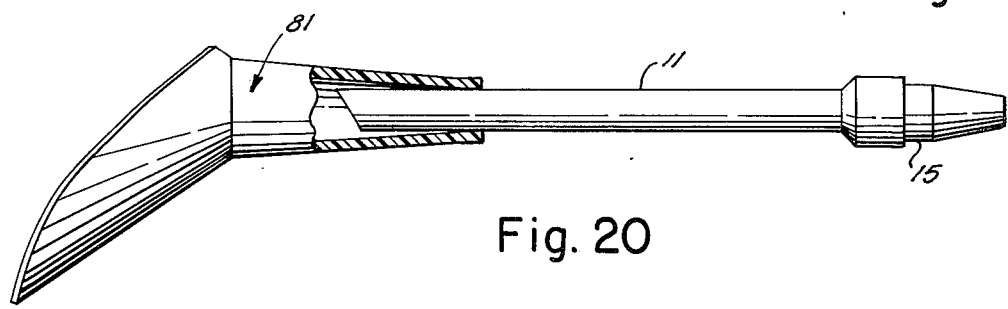
Figure 21:
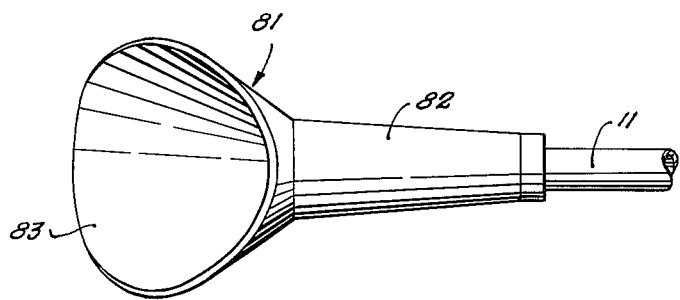
Figure 22:
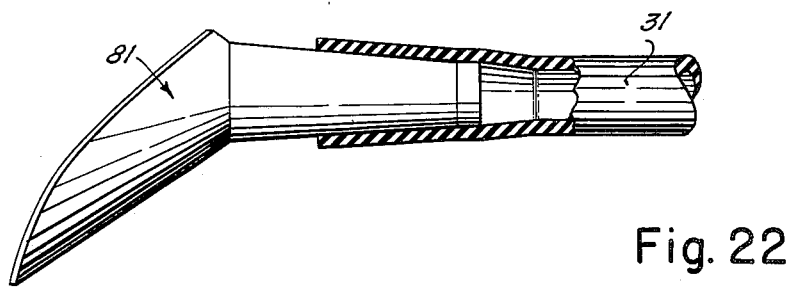
Figure 23:
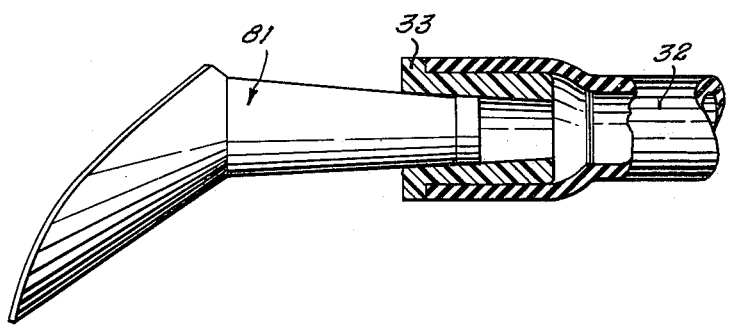

FIGS. 7 and 8 are sectional views taken respectively in the planes 7—7 and 8—8 of FIG. 6;

FIG. 9 is a fragmentary sectional view of a replaceable nozzle for the aspirator assembly of FIG. 1;

FIG. 9a is a fragmentary view of a base component as shown in FIG. 4 with an alternative form of adaptor tip;

FIG. 10 is a fragmentary detail view of the adaptor tip of FIG. 1, attached to a larger diameter suction hose;

FIG. 11 is a fragmentary sectional view of the adaptor tip of FIG. 1 attached to a standard ½ inch I.D. hose by means of an adaptor;

FIG. 12 is a detail view of a handle to be held in a user's hand for use with an aspirator;

FIG. 13 is a sectional view of a modified form of aspirator assembly including an air or wash water delivery feature;

FIG. 14 is a sectional view taken in the plane 14—14 of FIG. 13;

FIG. 15 is a fragmentary detail sectional view of the valve assembly of FIGS. 13 and 14;

FIGS. 16 and 17 are sectional views taken in the planes 16—16 and 17—17 respectively of FIG. 15;

FIG. 18 is a side elevation view, partially in section, of another aspirator assembly according to the invention;

FIG. 19 is a sectional view taken in the plane 19—19 of FIG. 18;

FIG. 20 is a side elevation view partly in section of another aspirator assembly according to the invention including a large area tip component and a supporting base component;

FIG. 21 is another view of the assembly of FIG. 20;

FIG. 22 is a side elevation view partly in section of the aspirator of FIG. 20 attached to a larger hose; and FIG. 23 is a side elevation view partially in section of the aspirator of FIG. 20 attached to a ½ inch hose by means of an adaptor.

DESCRIPTION OF THE PREFERRED EMBODIMENTS

In the following there are described several forms of aspirators according to the invention. In some of the aspirator assemblies to be described, certain elements may have a duel function; that is, one element may function as a base component for an assembly and also have the capability of functioning independently as a different form of aspirator.

In general the parts to be described are fabricated preferably of stainless steel. Certain parts will be preferably constructed from plastic materials, and these will be indicated; and of course the illustrated flexible conduit may be of rubber or rubberlike materials.

Embodiment of FIGS. 1 through 9a

One form of aspirator assembly 10 is illustrated in FIGS. 1, 2 and 6, and consists of three basic components namely a base or handle 11 illustrated in FIG. 4, tip 12 illustrated in FIG. 5, and a plunger 13 illustrated in FIG. 3.

The base 11 consists of a tubular member having a ¼ inch I.D., and having an adaptor tip 15 at one end for coupling the base to several sizes of flexible hose as will be described; and this adaptor tip may be secured to the base in any suitable manner such as soldering.

The tip component 12 is formed generally of tubular stock having a ¼ inch OD and having a nozzle 17 at one end formed at an angle and reducing in diameter. A finger ring 18 is secured to the tip 12 adjacent to the opposite end; and an elongated longitudinal slot 19 is formed in the tube adjacent to an opening to the opposite end, on the opposite side of the tube from the finger ring 18. The tip 12 then is dimensioned for a sliding fit within the base 11 so that these parts may be normally retained together but readily assembled and disassembled.

The plunger 13, as best seen in FIGS. 3 and 6, includes a tubular body dimensioned to be received within the tip component 12, but having an enlarged end 20 of about ¼ inch OD to be received within the base 11 with a sliding friction fit. At the opposite end, the plunger terminates in an elongated flexible stylet 21, which may in turn terminate in an enlarged end. Intermediate its ends, the plunger is provided with a laterally extending push button 22 which, in assembled relation, extends through the slot 19 in the tip component. In assembled relation, a portion of the slot 19 is exposed to permit limited reciprocating movement of the plunger relative to the tip. In the forward position illustrated in FIG. 6, the stylet 21 extends slightly beyond the nozzle 17 to remove any particles of tooth or bone which might become lodged in the tip and block the passage. In the retracted position illustrated in FIGS. 1 and 2, the stylet is withdrawn to permit flow of air through the entire aspirator assembly.

FIG. 9 illustrates an alternative form of nozzle 17a for the tip component 12, this nozzle being a separate part threaded onto the tip component.

As mentioned all of the parts are readily disassembled for cleaning; and the sliding friction fit between the base, plunger and tip provide a continuous sealed path between the nozzle 17 and the adaptor tip 15.

Adaptor Tip and Adaptor

One form of adaptor tip 15 is particularly illustrated in FIGS. 4 and 6 in relation to the base 11 which may also function as a unitary aspirator; and for this use the opposite end 11a terminates in a slanted transverse plane to define a nozzle. As best seen in FIG. 6 the aspirator tip is an elongated, generally tubular member about 1 inch in length, having a principal ID of ¼ inch and having a 5/16 inch counterbore at one end to receive the end of the base tube 11. The external configuration of the adaptor tip is important in relation to its function of coupling to flexible hoses of several different sizes, which are commonly used in the air and vacuum facilities provided in medical office buildings. References will be made herein to small hose, intermediate hose, and large hose, identified as follows: (1) small hose 30 as illustrated in FIG. 6 having a nominal ¼ inch ID; (2) intermediate hose 31 as illustrated in FIG. 10 having a nominal 5/16 inch ID; and large hose 32 as illustrated in FIG. 11 having a nominal ½ inch ID.

Referring now to the adaptor tip external configuration, as best seen in FIG. 4, the tip includes a large diameter axially extended, proximal end 25 of 7/16 inch diameter for example, an intermediate generally cylindrical portion 26 having a ⅜ inch diameter for example, and a distal tapered end 27 tapering from the intermediate portion 26 to a minimum diameter of about 5/16 inch. The intermediate portion 26, which may have a length of about ¼ inch for example, may also be provided with a slight taper of from 0.002 to 0.003 inches over its length enlarging from the distal toward the proximal end of this portion, for the purpose of seating this adaptor tip 15 in a handle to be described.

Referring now to FIG. 6, a small hose 30 is secured to the adaptor tip 15 by slipping the end of the hose over the tapered end 27, and the hose may be retained on the tapered portion particularly if the tapered portion is rough to some extent. For more tight securing of this hose, it may be slipped further on the adaptor over the intermediate portion 26.

Referring to FIG. 10, an intermediate hose 31 is slipped over the large diameter end 25 of the adaptor tip and is retained in this manner.

The securing of the large hose 32 is illustrated in FIG. 11 and this involves the use of an adaptor 33, which is a tubular sleeve preferably fabricated of a plastic material and having a radial flange at one end referred to as the distal end. The sleeve OD is about ⅝ inch so that it may be received within the large hose 32 which then enclosed the sleeve up to the flange. This adaptor has an internal bore which is slightly tapered from a larger diameter at the distal end to a smaller diameter at the proximal end, with the nominal diameter being about 7/16 inch so that it will receive the large end 25 of the adaptor tip 15 with a locking friction fit. The adaptor 33 then, functions to couple the large hose 32 to the adaptor tip 15. The broken lines in FIG. 11 illustrate the different positions which the adaptor would assume as the adaptor bore becomes enlarged in use.

FIG. 12 illustrates an extension handle 36 which may be convenient for use with a relatively short aspirator such as the base 11 illustrated in FIG. 4. As mentioned above this base 11, which is part of the aspirator assembly 10, may also be used apart from this assembly as an independent aspirator having a relatively large opening. The handle illustrated in FIG. 12 consists of a metallic tubular member having an ID of about ⅜ inch and having an OD of about 7/16 inch. The handle is provided with a knurled portion 37 intermediate its ends for convenience in holding the apparatus by the user. The ID of the handle coacts with the slightly tapered intermediate portion 26 of the adaptor tip 15 for a locking fit; and the opposite end of the handle may be connected to a large hose by means of the above described adaptor 33, as illustrated in FIG. 12. Alternatively, an intermediate hose 31 may be slipped over the end of the handle 36.

FIG. 9a illustrates a modified form of adaptor tip 15a which includes the large proximal end 25a and a tapered distal end 27a as above described but wherein the intermediate portion 26a includes a reduced diameter groove to assist in securing the small hose 30.

Embodiment of FIGS. 13 through 17

FIGS. 13 through 17 illustrate another form of aspirator assembly 13 which includes the features of the assembly 10 and some additional features namely provisions for providing wash water. As best seen in FIG. 13 this assembly includes a base 41, an tip component 42 and a plunger 43, all very similar to corresponding components of the assembly 10 except that the finger ring 18 is eliminated. An adaptor tip 15 is secured to the base 41. These corresponding components function in the manner described with respect to the assembly 10. The base 41 is enclosed within an enlarged housing 44, preferably fabricated of metal, and which is so shaped to provide a convenient handle to be held in the hand of the user, and which is suitably secured to the base member by means of soldering for example.

A push button valve assembly 45 is mounted within the housing and is connected to a water inlet fitting 46 at the rear of the housing by means of a conduit 47. The inlet fitting is adapted for connection to a water supply hose 48. A water discharge conduit 49 is secured along the tip component, by means of soldering for example, terminating adjacent the distal end, with its proximal end having a coupling fit with an outlet conduit 50 secured to the valve assembly and opening to the forward end of the housing 44.

The valve assembly 45, as best seen in FIG. 15, includes an external housing 52, which is threaded into the housing 44, and an internal housing 53 threaded into the external housing 52. An annular gasket 54 provides a seal between the internal and external valve housings, intermediate the ends, separating inlet and outlet ends of the external housing which communicate with the conduits 47 and 50 respectively. An elongated plunger assembly 55 includes a push button 56 projecting from the external housing 52 at one end, and a valve closure member 57 at the other end which bears against an annular seat 58 defined by the lower opened end of the internal housing 53. The internal housing includes wall openings to communicate the interior of this housing with the external housing above the annular seal 54. A compression spring 59 within the interior housing urges the plunger assembly 55 upward to normally seat the valve and break communication between the conduits 47 and 50. Pressure on the push button 56 opens the valve to effect the flow of water from the discharge conduit 49.

Embodiments of FIGS. 18 through 23

FIGS. 18 and 19 illustrate another simplified form of aspirator assembly 70 which includes the base 11 with its associated adaptor tip 15, and a tip component 71 consisting of an elongated tubular member having a ¼ inch OD for sliding friction fit within the base member 11. A nozzle end of the tip component is provided with openings 72 in the side wall adjacent to the end to provide vent openings permitting flow of air therethrough in the event the tip end is sealed by tissue. This avoids injury or damage to the tissue, and this assembly 70 may be referred to as a "no-stick" aspirator.

FIGS. 20 and 21 illustrate another form of aspirator assembly 80 consisting of the base 11 and a large area tip component 81 designed for removal of mist. The tip 81 includes a tapered shank 82 defining the proximal end and having an ID of about 5/16 inch for a sliding friction fit with the OD of the base 11. The distal end is a diverging funnel-like member terminating in a generally planar opening at an angle to the longitudinal axis of the aspirator. As mentioned, this tip is useful to withdraw cooling water spray or mist from the mouth for example.

FIG. 22 illustrates the large area aspirator tip alone being coupled to an intermediate hose 26, with the OD of the tip shank 82 at its proximal end being about 7/16 inch to be received within the intermediate hose.

FIG. 23 illustrates the same large area tip component 81 with its shank received within the bore of an adaptor 33 for coupling to a large hose 32.

What has been described are a number of forms of aspirators which include a particular form of adaptor tip designed for enabling the coupling of the aspirators to three different sizes of hose which are fairly standard in utility services provided in medical buildings With such adaptor tip, the aspirators are readily employed by customers, such as dentists and oral surgeons, regardless of the particular type of utility service provided in the building with respect to the size of suction hose.

Also described are different forms of aspirators, which are adapted to different uses, and some of which are adapted to multiple uses.

While preferred embodiments of the invention have been illustrated and described, it will be understood by those skilled in the art that changes and modifications may be resorted to without departing from the spirit and scope of the invention.

What is claimed is:

1. Aspirator apparatus comprising
an elongated tubular member including an adaptor tip at one end; said adaptor tip having a smaller diameter portion at its distal end, and having an axially extended, cylindrical enlargement spaced from said distal end; said smaller diameter portion including a tapered portion reducing in diameter toward its end, and adapted to be received and retained in a small diameter resilient flexible conduit;
a tubular adaptor, having a slightly tapered internal bore dimensioned in relation to said cylindrical enlargement for frictional coupling therewith; said adaptor having an outer diameter adapted to be received and retained in a large diameter flexible conduit, and having an external radial flange at one end; said tapered bore being larger at the flanged end of said adaptor and smaller at the opposite end;
a tip component comprising an elongated tubular body, having a nozzle at one end and having a longitudinal slot in one wall opening to its other end;
said tubular member defining a base component; said tubular member other end having an inner diameter dimensioned relative to the outer diameter of said tip body for a mating friction coupling;

a plunger comprising a tubular body, a flexible stylette fixed to one end of said body to extend into said nozzle, and a boss projecting radially from said body; said plunger body having a portion dimensioned relative to the inner diameter of said tip component body, forward of said longitudinal slot, for a sliding sealing fit therewith; said plunger body having an end portion, remote from said stylette, dimensioned relative to the inner diameter of said base component for a sliding sealing fit therewith; said plunger body, in assembly, disposed with said boss projecting through said tip component slot, whereby said plunger is reciprocable by said boss to reciprocate said stylette relative to said nozzle; and said plunger body defining a conduit to bridge said slot.

2. Aspirator apparatus as set forth in claim 1
said adaptor tip cylindrical enlargement having a diameter of about 7/16 inch to be frictionally coupled within said tubular adaptor having a tapered bore of nominal 7/16 diameter.

3. Aspirator apparatus as set forth in claim 2
said adaptor tip tapered portion reducing to a minimum diameter of about 5/16 inch to be received in a resilient flexible conduit having an inner diameter of about ¼ inch.

4. Aspirator apparatus as set forth in claim 1
said adaptor tip smaller diameter portion including an intermediate cylindrical portion between said enlargement and said tapered portion;
an elongated tubular handle member having an inner diameter dimensioned relative to said adaptor tip intermediate cylindrical portion for a friction fit therewith, and having an outer diameter dimensioned relative to said adaptor tapered bore to be received within said bore with a friction coupling fit.

5. An aspirator tip assembly comprising
an elongated tubular base member, having an adaptor tip at one end for coupling said base member to a flexible conduit; said adaptor tip having a smaller diameter portion at its distal end and a larger diameter portion at its proximal end to enable coupling of said base member to conduits of different size;
an aspirator tip comprising an elongated tubular body, having an aspirator nozzle at one end and having a longitudinal slot in one wall opening to its other end; said tip other end and the other end of said base member being dimensioned relative to each other for a mating friction coupling;
a plunger comprising a tubular body, a flexible stylette fixed to one end of said body to extend into said nozzle, and a boss projecting radially from said body to extend through said aspirator tip slot, to enable reciprocation of the plunger relative to said aspirator tip to selectively extend said stylette to the tip of said nozzle; said plunger body having a portion dimensioned relative to the inner diameter of said aspirator tip body for a sliding sealing fit therewith; and said plunger body having an end portion, remote from said stylette, projecting from said aspirator tip body and dimensioned relative to the inner diameter of said base member for a sliding sealing fit therewith;
enlarged housing means fixed to and generally enclosing said base member defining a handle to be gripped by the user; an on-off valve mounted on said housing for manipulation by the user, said valve communicating an inlet conduit having a termination projecting from said housing adjacent to said adaptor tip and an outlet conduit opening from said housing at the opposite end;
said aspirator tip having a discharge conduit disposed in generally parallel relation therewith terminating in a discharge end adjacent to the nozzle of the aspirator tip, and having its other end disposed for coupling to said valve outlet conduit.

6. An aspirator tip assembly as set forth in claim 5
said valve assembly including a push button closure member having resilient means normally urging the closure member to the outer position to shut off the flow of water to said discharge conduit.

* * * * *